(12) United States Patent
Föglein

(10) Patent No.: US 7,976,882 B2
(45) Date of Patent: Jul. 12, 2011

(54) DEMUCILAGED FLAX SPROUTS AND THEIR BY-PRODUCT AS WELL AS PRODUCTION AND APPLICATION THEREOF

(76) Inventor: Ferenc Föglein, Budapest (HU)

( * ) Notice: Subject to any disclaimer, the term of this patent is extended or adjusted under 35 U.S.C. 154(b) by 213 days.

(21) Appl. No.: 11/991,370

(22) PCT Filed: Sep. 6, 2005

(86) PCT No.: PCT/HU2005/000095
§ 371 (c)(1),
(2), (4) Date: Mar. 3, 2008

(87) PCT Pub. No.: WO2007/029045
PCT Pub. Date: Mar. 15, 2007

(65) Prior Publication Data
US 2009/0155397 A1    Jun. 18, 2009

(51) Int. Cl.
*A61K 36/55* (2006.01)
*A23L 1/36* (2006.01)
*C08B 37/00* (2006.01)
*C12N 1/20* (2006.01)

(52) U.S. Cl. ......... 424/768; 426/629; 426/44; 435/274; 435/253.6

(58) Field of Classification Search .................. None
See application file for complete search history.

(56) References Cited

U.S. PATENT DOCUMENTS

| | | | |
|---|---|---|---|
| 3,684,790 A | 8/1972 | De Carranza | |
| 5,266,473 A * | 11/1993 | Nielsen | 435/219 |
| 6,929,796 B1 * | 8/2005 | Conti-Fine | 424/185.1 |
| 6,955,831 B2 * | 10/2005 | Higgs et al. | 426/630 |
| 2002/0059660 A1 * | 5/2002 | Tricoli et al. | 800/280 |
| 2003/0134006 A1 | 7/2003 | Chukwu | |
| 2004/0191396 A1 * | 9/2004 | Barker | 426/629 |

FOREIGN PATENT DOCUMENTS

| | | | |
|---|---|---|---|
| GB | 1 313 285 A | 4/1973 | |
| JP | 55-165902 A | 12/1980 | |
| WO | WO-03/003854 A | 1/2003 | |
| WO | WO-2004/060072 A | 7/2004 | |
| WO | WO-2005/012342 A | 2/2005 | |

OTHER PUBLICATIONS

Ravenna et al, Significance of mucilages in the germination of seeds, Scienze Fisiche, Matematiche e Naturali, Rendiconti (1911), 19 (II), 247-52.*
Alzueta et al, Effects of removal of mucilage and enzyme or sepiolite supplement on the nutrient digestibility and metabolyzable energy of a diet containing linseed in broiler chickens, Animal feed science and technology 97 (2002) 169-181.*
Wanasundara et al, Removal of flaxseed mucilage by chemical and enzymatic treatment, Food chemistry, 59 (1): 47-55, 1997.*
Mazza G et al., Journal of Food Science, Institute of Food Technologists, vol. 54, No. 5, Sep. 1, 1989, pp. 1302-1305.
Wanasundara P K J P D et al., Food Chemistry, vol. 59, No. 1, 1997, pp. 47-55.
Alzueta C et al., British Poultry Science, vol. 44, No. 1, Mar. 2003, pp. 67-74.
Kalac J., Rexova L.: Biochimica et Biophysica Acta, vol. 167, No. 3, Nov. 19, 1968, pp. 590-596.
Mazza G et al., Journal of Food Science, Institute of Food Technologists, vol. 54, No. 5, Sep. 1, 1989, pp. 1302-1305.
Wanasundara P K J P D et al., Food Chemistry, vol. 59, No. 1, 1997, pp. 47-55.
Alzueta C et al., British Poultry Science, vol. 44, No. 1, Mar. 2003, pp. 67-74.
Kalac J., Rexova L.: Biochimica et Biophysica Acta, vol. 167, No. 3, Nov. 19, 1968, pp. 590-596.

* cited by examiner

*Primary Examiner* — Qiuwen Mi
(74) *Attorney, Agent, or Firm* — Birch, Stewart, Kolasch & Birch, LLP

(57) ABSTRACT

The present invention relates to demucilaged flax sprouts derived from flaxseeds freed of their mucilage. The flax sprouts according to the invention are easily digestible and can be utilized in different fields, e.g. in food industry, therapy and hus-handry. The invention also relates to the production process and applications of the demucilaged flax sprouts. The present invention further relates to a process for recovering mucilaginous substance generated as a by-product in the production process as well as to various applications thereof.

14 Claims, No Drawings

DEMUCILAGED FLAX SPROUTS AND THEIR BY-PRODUCT AS WELL AS PRODUCTION AND APPLICATION THEREOF

FIELD OF THE INVENTION

The present invention relates to demucilaged flax sprouts easy to digest, suitable for direct human consumption and utilizable in different fields such as in food industry, therapy and animal husbandry. The invention also relates to the production process and applications of the demucilaged flax sprouts. The present invention further relates to a process for recovering mucilaginous substance originating as a by-product in the production process as well as to various applications thereof.

BACKGROUND OF THE INVENTION

The flax is a highly nutritious plant. It could be advantageously utilized in human nourishment on account of its high protein and oil content. Compared to other nutritive material sources it is the flax that contains the greatest amount of unsaturated fatty acids including alpha-linolenic acid of type omega 3 which is essential for the human organism [see Table 1; Bene et al.: "Szappanok és mosószerek" (Soaps and detergents), Müuszaki Könyvkiadó, Budapest, 1957].

utilisation of the flaxseed, is however, for many reasons, very limited.

The reasons for this situation can be summarized as follows.

1. The oil content of flaxseed can reach 40-50% and the oils occurring in this oil content belong to the so-called drying oils. Because a considerable part are unsaturated their melting points are very low, and because they are unsaturated they react very quickly with the oxygen in the air and quickly become rancid. Because of the rancidity a so-called "varnish" taste develops which makes the flaxseed less suitable for human consumption. Though by milling of the flaxseed the active ingredients become accessible, the milled product, is however, difficult to store and the amount of essential fatty acids of type omega 3 decreases already during the milling.

2. Another property greatly limiting the application of flaxseed is that it contains in the outer surface of the seed husk a very complicated, pectin-like material with a composition unknown up to now. The role of this material is to protect the seeds passing through the digestive tract of an animal that they may remain viable. Similarly, the human digestive tract is also unable to digest the raw, untreated seed, 1 kg flaxseed is able to bind 5 litres of

TABLE 1

Average percentage distribution of the fatty acids of more important fats

| | Saturation | | | | | | | | | | |
|---|---|---|---|---|---|---|---|---|---|---|---|
| | Saturated acid | | | | | | | Unsaturated acid | | | |
| | Number of carbon atoms | | | | | | | | | | |
| | 12 | 14 | 16 | 18 | 20 | | 18 | 18 | 18 | 18 | 22 | |
| | | | | | | The name of fatty acid | | | | | | |
| | Lauric | Myristc | Palmitic | Stearic | Arachic | Others | Oleic | Linolic | Linolenic | Ricinoleic | Erucidic | Others |
| Coconaut oil | 63 | 18 | 8 | 3 | | | 6 | 2 | | | | |
| Palmnut oil | 57 | 15 | 8 | 2 | | | 17 | 1 | | | | |
| Mutton tallow | | 5 | 25 | 31 | | 2 | 36 | 1 | | | | |
| Beef tallow | | 3 | 28 | 20 | 1 | 2 | 44 | 2 | | | | |
| Pork fat | | 1 | 28 | 12 | | | 48 | 6 | | | | 5 |
| Bone fat | | | 20 | 19 | | | 55 | 6 | | | | |
| Palm oil | | 4 | 38 | 4 | | | 46 | 8 | | | | |
| Olive oil | | | 10 | 2 | | | 80 | 8 | | | | |
| Castor oil | | | | 4 | | | 8 | 2 | | 86 | | |
| Groundnut oil | | | 7 | 4 | 6 | | 62 | 21 | | | | |
| Rapeseed oil | | | 2 | 2 | | | 26 | 18 | 2 | | 50 | |
| Rice germ oil | | | 18 | 2 | | 1 | 47 | 28 | | | | 4 |
| Sesame oil | | | 10 | 2 | | | 49 | 39 | | | | |
| Cotton-seed oil | | 1 | 22 | 2 | | | 28 | 45 | | | 2 | |
| Soybean oil | | 1 | 7 | 5 | | | 26 | 55 | 6 | | | |
| Grape-seed oil | | | 6 | 2 | | | 37 | 55 | | | | |
| Corn oil | | | 8 | 4 | | | 46 | 42 | | | | |
| Pumpkin-seed oil | | | 13 | 6 | | | 37 | 44 | | | | |
| Tomato-seed oil | | | 15 | 7 | | | 16 | 62 | | | | |
| Sunflower oil | | | 4 | 2 | | | 38 | 56 | | | | |
| Linseed oil | | | 10 | | | | 9 | 37 | 44 | | | |

The flax seed, as far as the composition of the contained nutritive materials is concerned, has excellent properties [see: USDA National Nutrient Database for Standard References, Release 17 (2004)]. Furthermore, it contains phyto-hormones (lignans) in great quantity which certifiably have anticancer effect (see e.g.: Carcinogenesis 20(9): 1831-1835, 1999; Nutr. Cancer 43(2): 187-192, 2002). On the basis of the properties of the contents it is desirable that the flax should be an integrated part of the nutrition and it should be utilised in the food industry in a wide range. For the time being the water in consequence of which the gastric juice is not able to reach the surface of seed husk, and this slippery, gel-like material significantly enhances the intestinal activity, and functions as a purgative substance in countless cases. The internal content of the seed cannot, however, be utilized.

3. Furthermore, it is known that the mucilage of the flaxseed contains a lot of materials hindering the digestion, e.g. hydrocyanids and trypsine inhibitors. Though their effect can be decreased by heat treatment, their hindering effect cannot be completely eliminated (Journal of the American Oil Chemists' Society 70(9): 899-904, 1993). For this reason the removal of mucilage should be very desirable to ensure better digestion and absorption.

Of course, lots of attempts have been made to eliminate the above mentioned problems. One such programme is mixing flax seed into the fodder of domestic animals, and by subsequently consuming and digesting the meat of animals bred on flax seed a person will be able to absorb the essential fatty acids. The effectiveness of this method, however, is very low, and what is more, the meat of the animals can have a "varnish" taste as a consequence of the rancidity. In another attempt, flax seed is mixed to the bakery products. In this case the mucilaginous materials are not damaged during the bake and the seeds remain undigested, their advantageous effect to the intestines remains only as fibres.

We have to mention that there have been a lot of attempts in connection with the removal of mucilage from the surface of flaxseed. Kalac J. and Rexova L. (Biochim. Biophys. Acta 167(3): 590-596, 1968) applied the mucilage as a test material to characterize an enzyme isolated from *Aspergillus niger*; during this experiment they worked with a mucilage available in trade. Though the aim of their experiments was absolutely different from the aim of the present invention, their results showed that the pectin-like mucilage of flaxseed can be partially disintegrated. Wanasundara P. and Shahidi F. (Food Chemistry 59(1): 47-55, 1997) used an enzymatic process in order to promote the protein digestion of flax meal obtained through milling of the flax seed. In this process the flax seed mucilage was only partially removed and the possibility of sprouting was excluded.

Another remarkable attempt relates to the feeding of broiler chickens (Br. Poult. Sci. 44(1): 67-74, 2003). Alzueta R. et al. reported that the inclusion of whole flax seed (with the mucilage) milled together in the chicken feed resulted in a mass reduction instead of mass growth in spite of the fact, that the nutritive value of the flaxseed is very high. Including milled flaxseed with reduced mucilage content to the feed, however, improved the utilization. It should also be noted that in this case only a partial removal of mucilage (about 83%) is reached so the results do not reflect a complete utilization. Moreover, the acidic removal of the mucilage and the high temperature applied (80° C.). cause the seeds to loose viability and cannot germinate.

From the point of view of the preservation of active ingredients the most successful procedure is the sprouting of the flax seeds. It is known that the oil present in large quantities in the living seedlings does not become rancid, and the valuable active ingredients are presumably protected against external oxidation processes as they are enclosed into micelles. At present the sprouting of flax seeds, however, has considerable limits. The gel-like material surrounding the husk (so-called mucilage) prevents direct sprouting and the external sterilization of seeds, which is the precautionary measure necessary for distribution. This is why it is necessary to use roundabout solutions. The seeds can, for example, be sprouted on some kind of carrier material (soil layer, cotton fabric, diaper material, etc.), and the green parts of plants can be consumed only by harvesting the cotyledonous plants. This application, however, is very elaborate, and its application is not suited for large scale production. Another disadvantage is the fact that when the cotyledons become green, already significant energy has been drawn from the seed, the development of bitter tastes starts, and the decomposition of multiple unsaturated fatty acids begins, resulting in a limited storability of the plant material (10-12 days).

In the patent publication document No. WO 03/003854 Barker D. et al. introduced a sprouting process in order to increase the relative amount of alpha-linolenic acid in the sprout product. In addition to the fact that we were not able to repeat these results, the aim of the procedure reviewed in the mentioned patent publication document No. WO 03/003854 was not the removal of mucilage hindering the digestion, and does not solve that problem at all. Though the composition of the sprout material was improved with this introduced method, it is very likely that the absorption of these compounds does not happen in the animal and human organism. Furthermore, the method elaborated by Barker D. et al. does not allow for the surface sterilization according to the requirements of food-hygiene.

The flax seed mucilage is by itself an interesting and valuable material. A lot of articles dealt with its investigation (see e.g.: Journal of Food Science 54(5): 1302-1305, 1989; Food Hydrocolloids 17(2): 221, 2003; Chromatographia 58(5-6): 331-335, 2003). The flax seed mucilage is indigestible for the human organism, therefore this material is called water-soluble fibre material (Philips G. O., Food Hydrocolloids 17(2): 221, 2003). According to experiences this material forms a thin layer on the stomach wall and the villi; this layer has both a strong laxative effect, and also prevents the absorption of nutritive substances. Thus it can be utilized as an additive for slimming agents.

The aim of present invention is to eliminate the above-mentioned problems and to bring the flaxseed into a suitable form for direct human consumption. We have found that this aim can be reached by removing the mucilage from the surface of flax seed. Through this process the flax seeds are deprived of mucilage, and then the seeds are germinated. The sprouted flax seed become accessible for the gastric juices, and the hard to digest oils are mobilized in the sprouting flaxseed. The flax sprout thus becomes suitable for direct human consumption or can be utilized as a basic food material. A further aim was to preserve the vitality of the seeds in order to retain their ability to sprout and also to gain access to their inherent values.

Thus, the objective of the present invention has been to work out a process suitable for completely removing the gel-like mucilage from the surface of the flax seed and thereby to make the surface of flax seed suitable for direct sterilization and sprouting.

The composition of mucilage surrounding the flaxseed is only partially known, this problem is not completely solved yet. Anyway, a complex molecule with a very complicated composition is in question, the removal and decomposition of which presents a problem so far unresolved. The results till now show only the fact that there is an enzyme which begins the partial decomposition of mucilage. During our experiments it was proved that in the case of different cultivated flax varieties the composition of mucilage can vary considerably from variety to variety as they react to the enzymatic treatment in a very different ways.

The mucilaginous material from the flax seed steeped in water could not be removed by washing, pressing and intensive agitation. The expression "removal" means an almost 100% removal, as the seeds can be sterilized only in this way. On the basis of this fact it is presumed that the mucilaginous material has a stable gel structure, and that this structure is stabilized with cross-links. Surprisingly the enzymatic treatment of flax seeds steeped in water in advance does not give any result at all. The experiments of digestion directed to the gel from outside were unsuccessful; nevertheless, this method proved to be the most suitable from the point of view of retaining the sprouting ability.

We have found, however, that if the flax seeds are soaked in an aqueous enzyme solution containing at least one pectinolytic, cellulolytic and optionally proteolytic enzyme, the mucilage can be separated from the surface of seeds, and the seeds keep their viability. These results were not predictable on the basis of the prior art at all. The sprouting experiments showed that the husk deprived of mucilage is not injured by the enzymatic treatment (it is important because the lignans are bound to the husk), in fact, it is so stable that the seeds can be effectively sterilized prior to sprouting with sodium hypochlorite solution of high concentration. The flax sprout obtained in such a way is free from mucilage, easy to digest, suitable for direct human consumption and can be employed in a lot of different fields.

Under the effect of enzymatic treatment according to this invention the mucilaginous material separates from the surface of seed on a gentle mechanical influence as a thick, mucilaginous solution. According to our working hypothesis the cross-links of complex gel structure and links between the mucilage and the husk, respectively, split on the influence of enzymatic treatment. This is supported by our observation that the viscosity of the separated mucilaginous material does not change even after intensive incubation (lasting several days). This allows for further processing of the mucilaginous material separated from the flaxseed.

The separation of mucilaginous material enabled us to work out a quick method for the purification and formulation of this material. We have found that at a low temperature (4° C.) the mucilaginous material precipitates from the aqueous solution already at a 40% (v/v) alcohol concentration. Through repeated alcohol washing and heat treatment the materials hindering the digestion (hydrocyanids and inhibitors) are removed.

SUMMARY OF THE INVENTION

The invention relates to demucilaged flax sprouts derived from flax seeds deprived of mucilage. We have to mention that in the description the meanings of "mucilage" and "mucilaginous material" are the same.

The invention further relates to a process for the production of demucilaged flax sprouts through the following steps:
(i) treating flaxseeds with an aqueous enzyme solution containing at least one pectinolytic (pectin-splitting) enzyme and cellulolytic (cellulose-splitting) enzyme and optionally a proteolytic (protein-splitting) enzyme;
(ii) removing the mucilaginous material separated from the surface of flaxseeds during step (i);
(iii) cleaning the flax seeds obtained by step (ii) for mucilage by washing
(iv) sterilizing the flaxseeds obtained in step (iii); and
(v) sprouting the sterilized flaxseeds.

The invention further relates to a process for the recovery of mucilaginous material separated during the enzymatic treatment of flaxseed, comprising the precipitation of gel-like mucilaginous material separated with the process according to this invention from its aqueous solution with an organic solvent suitable for precipitation of polysaccharides, the dehydration, desiccation and pulverization of the mucilaginous material, and optionally processing it further. The invention further relates to the application of mucilaginous material obtained in this manner, first of all for cosmetic, pharmaceutical, microbiological and industrial purposes.

DETAILED DESCRIPTION OF THE INVENTION

In the process according to the invention the flax seed used as a basic material can be the seed of a flax variety, e.g. *Linum usitatissimum* cv. Brown, *L. usitatissimum* cv. Goldline and the like.

According to one preferred embodiment of the process of the present invention the aqueous enzyme solution of the desired composition can be prepared from the necessary enzymes. The seeds are swollen in the enzyme solution which is prepared beforehand. The flax seed may be placed in plastic bags with small holes or plastic net, the mesh of which is about 0.2 mm. The enzyme solution contains pectinolytic and cellulolytic and optionally proteolytic enzymes. As a pectinolytic enzyme pectinase, e.g. Macerozyme R-10 or a pectinase derived from *Aspergillus niger*, as a cellulolytic enzyme cellulase, e.g. Onozuka R-10, glucuronase, helicase or sulfatase; as a proteolytic enzyme lysosyme, protease and the like can be used. In a preferred embodiment of the invention a pectinolytic (pectin-splitting) enzyme is used together with a cellulolytic (cellulose-splitting), preferably pectinase derived from *Aspergillus niger* and glucuronase. According to another preferred embodiment, a pectinase is used together with lysosyme, which is well known to be a multifunctional enzyme. In another preferred embodiment, a pectinolytic enzyme is used together with cellulolytic enzymes, namely glucuronase and sulfatase. The aqueous enzyme solution contains the pectinolytic enzymes in 1-10 U/ml, preferably 1-5 U/ml concentration, the cellulolytic enzymes in 2-50 U/ml, preferably 5-15 U/ml concentration and the proteolytic enzymes in 10-500 U/ml, preferably 50-200 U/ml concentration. The composition of the enzyme solution depends on the flax variety.

According to another preferred embodiment the supernatants originating from fermentation broth of micro-organisms producing specific extracellular enzymes, as pectinolytic, cellulolytic and proteolytic enzymes, are used as aqueous enzyme solution. The supernatants are adjusted to pectinase enzyme activity. The fermentation broth can be originated from fermenting bacteria or fungi, e.g. *Trichoderma* sp., as *Trichoderma rosea, Glyociadium catenulatum* and the like. The mucilaginous material originated from the process according to this invention can be used as fermentation media, too. The fermentation broth is centrifuged, the supernatant is separated and optionally sterilized by sterile filtration, or by treatment with chloroform, and the like. The fermentation broth is optionally filtered to be cell-free. The application of fermentation broth as a natural source of enzyme in the process according to this invention allows the significant reduction of costs of the production, first of all the costs of the production on an industrial scale.

The pH of enzyme solution is mildly acid, preferably 6.5, which can be adjusted with organic or inorganic acids or with acidic salts. For this purpose hydrochloric acid, acetic acid or potassium dihydrogen phosphate, preferably acetic acid can be used. The seeds are treated with an enzyme solution of a volume ratio from one-and-a-half to two, preferably one-and-a-half parts calculated to one volume unit of the seeds. During this treatment the seeds take up the enzyme solution, then they are incubated at temperatures of 20-30° C., preferably 25-28° C. for 6-24 hours, preferably for 18-20 hours. Then the seeds are swollen to their water absorbing capacity (about fivefold of dry seed volume). The swelling can be promoted with a gentle mechanical agitation, preferably stirring. The aqueous, gel-like mucilaginous material is separated from the seeds by applying a mild pressure, preferably pressing to the wet seed volume. In this manner about 90% of the mucilaginous material can be separated. Because the sterilization of seeds is necessary for the germination, the rest of mucilaginous material has to be removed from the seeds. It can be achieved by an intensive watery washing. The washing of seeds is continued until the wash liquid turns transparent (not opalescent), and mucilaginous material cannot be detected in the wash liquid, neither by touch nor with a chemical method. Then the free water between flaxseeds can be removed by draining, vacuumsuction or centrifugation, and the seeds obtained in this manner are directly used for sprouting.

Then the seeds perfectly cleaned of their mucilage are sterilized. For this purpose different sterilizing agents e.g. sodium hypochlorite, hydrogen peroxide, hyamine and the like are used. The seeds are preferably sterilized in a sodium hypochlorite solution of low concentration for 30-50, preferably 40-45 minutes during continuous stirring, then the sterilizing agent is removed by washing with water, preferably by repeated washings, and the free water is removed by one of the above mentioned procedures. The seeds obtained in this manner are germinated by spreading them in a layer of 2-3 cm.

The germination can be carried out in the usual way, preferably in darkness, at temperature 18-30° C. for 6-48 hours. The humidity left on the seeds is sufficient for them to sprout. The sprouts are grown up to a length of about 1-5 mm, preferably 2-4 mm, then they are harvested and are used directly or after drying. The flax sprouts obtained in this way are free from mucilaginous material. This is proved by the fact that the liquid flowing out after repeated watery steeping of flax sprouts do not contain sugar-like materials after acid treatment. They can be stored well and can be utilized directly for consumption or in food preparations. It was found that for example by packing the sprouts in plastic foil, and storing them at a temperature of 4° C. for 60 days no loss in quality occurred, e.g. the original taste and consistency was preserved.

The objective of the preparation of industrial food products containing fresh flax sprout is that the flax sprout used as an additive should be kept in a active, not decayed condition for a time as long as possible. Our aim has been that the fresh flax sprout should preserve its original taste and consistency in the product. For this purpose it has to be taken into consideration that the temperature during the processing should not exceed temperature 40-45° C.; in this manner the premature decay of flax sprout and the oxidation of multiple unsaturated fatty acids can be prevented. Another very important point of view is, however, that the total osmotic pressure of food (in an aqueous medium, e.g. cheese), to which the flax sprout is added, should not exceed the isoosmotic value. In the case of high osmotic pressure the flax sprout looses water during the storage and its consistency changes.

For other applications the flax sprout can be dried and crushed, and the product obtained in this manner can be stored similarly as a kind of cereal, e.g. wheat or wheat meal. The drying is performed gently, preferably under temperature of 30° C. in such a manner that the flaxseed sprouts are dried to 75-90 percent of their initial seed weight, preferably to 80-85 percent of weight. The product obtained this way can be consumed as it is, or it can be mixed into food or animal fodders. For human purpose, it can be also used as a food supplement or nutriment or in a food preparation, first of all as a supply of essential fatty acids and phyto-hormones. For this purpose it can be used as instant granules together with auxiliary materials usually employed in the food industry or in the preparations of pharmaceuticals, as e.g. maltose, maltodextrine, binder materials, aroma materials, sweeteners, food colouring agents, etc., or together with materials usually employed in the preparation of nutriments, as e.g. protein, carbohydrate, minerals, vitamins, etc., or it can be pressured to tablets or encapsulated in a manner known per se.

One of the advantages of the process according to the invention is that the flax sprout obtained in this manner is free of mucilage and therefore likely to be absorbed well, and its valuable components can be utilized in the living organisms.

Another advantage of the process according to the present invention lies therein that 90% of the separated mucilaginous material originating as a by-product can be recovered and utilized. The squeezed, concentrated mucilaginous material can be precipitated with organic solvents suitable for precipitation of polysaccharides, thus, e.g. it can be precipitated with alcohols or chloroform. The squeezed, concentrated mucilaginous material is precipitated preferably in 50% (v/v) aqueous ethanol solution at a temperature of 4° C. after leaving it at rest for at least 12 hours, and it can be separated well by centrifugation. The precipitating agent (e.g. ethanol) can be recovered from the filtrate. The precipitate obtained by centrifugation can be dehydrated with 96 percent ethanol, and the dehydrated precipitate is centrifuged again, then the precipitate obtained in this manner is dried. At the end of this process an amorphous material is produced which can be pulverized and packed. The flax mucilaginous material obtained in this manner can be perfectly dissolved again in water.

The mucilaginous material obtained by this process can be utilized in many fields. It can be utilized in cosmetic agents, e.g. in body lotions as an emulsifying agent and foaming material. It can be also utilized for food industrial purposes as a consistency improver. It can be used in microbiological processes as a culture medium or as a component of culture media for the cultivation of pectinolytic micro-organisms and/or micro-organisms utilizing polysaccharides, e.g. *Aspergillus niger* or Glyocladium catenulatum. In fact, it can be employed as a lubricant with a water basis for e.g. lubrication of rotating instruments.

The advantages of invention can be summarized as follows.

The demucilaged flax sprout according to the invention eliminates the hindering factors which obstructs the possibility of utilizing of the flax seed in the food industry and in other fields. The demucilaged flax sprout does not contain materials hindering the digestion and preventing the absorption of nutrients. The demucilaged flax sprout can in a dried form and in a form of a grist respectively be stored for a long period without refrigeration, similar to the products made from cereals. The demucilaged flax sprout according to the invention can be popular because the valuable active ingredients and taste materials are biologically protected and they do not change during storage.

The method worked out for the preparation of demucilaged flax sprout makes it possible completely to mechanize the process and allow for a large scale production. In consequence of this fact new products having high biological value can appear in the food- and fodder market and also among the pharmaceutical products.

Additionally, according to the invention there is a possibility to process the flaxseed without any loss during the preparation of flax sprout since the by-product obtained can be utilized further.

The invention is illustrated with the following examples which, however, are not to be considered as limiting the invention disclosed herein.

EXAMPLE 1

Demucilaging of Flaxseed

The seeds of variety *Linum usitatissimum* cv, Brown with high sprouting ability, purified for food industrial purposes (1 kg) are placed into a 10 litre plastic bag (similar to dense weaved curtain material) with meshes of 0.2 mm. The bag is placed in closed form into 1.5 litres enzyme solution, contains the followings: 2% Macerozyme R-10 (manufacturer: Kinki Yakult MFG Co., Japan), 0.5% Cellulase "Ozonuka" R-10 (manufacturer: Kinki Yakult MFG Co., Japan) and 1500 ml tap water, pH 6.5 which is adjusted by 1N acetic acid. The seeds are gently agitated up till the time as the total amount of liquid will be absorbed (generally 20-30 minutes). At this time the seeds generally settled into one block. The seeds together with the bag are incubated at 25° C. for 24 hours. After the expiry of incubation periods the bag containing the seeds is placed into lukewarm water, and applying gentle agitation the seeds are allowed to be perfectly saturated with water. Then the bag is placed in a press and is pressed to seed volume with mild pressure (e.g. with a wine-press). In consequence of the pressing 90% of mucilaginous material can be separated. This compressed material is suitable to further processing. The rest of mucilaginous material is washed out from the seeds and the bag, respectively, by intensive washing in running water, for about 15 minutes. The washing of seeds is continued until the flowing liquid is no longer opalescent, and mucilaginous material cannot be detected by touch. To allow sterilisation no traces of mucilaginous material may remain on the surface of the husk. The free water is drained from the demucilaged seeds in the bag, then the seeds are used for further processing.

EXAMPLE 2

Demucliaging of Flaxseed

The process is practically the same as in Example 1, but the seeds are soaked in an enzyme solution with the following composition:

3 U/ml Pectinase (from *Aspergillus niger*) (Serva)
10 U/ml Glucuronase (industrie Biologisque Francais SA)
30 U/ml Sulfatase (Industrie Biologisque Francais SA).

In the case of the above described combination the seeds have to be incubated at higher temperature, 28° C., to obtain similar results.

EXAMPLE 3

Demucilaging of Flaxseed

The seeds of variety *Linum usitatissimum* cv, Goldenline 90 with high sprouting ability, purified for food industrial purposes (1 kg) are placed into a 10 litre plastic netbag with perforations of 0.2 mm. The bag is placed in closed form into 1.5 litres enzyme solution. The composition of enzyme solution is the following:

2 U/ml Pectinase (from *Aspergillus niger*) (Fluka)
100 U/ml Lysosyme (from egg white) (Fluka)
pH 6.5 adjusted by $KH_2PO_4$.

The incubation is performed according to Example 1. After expiry of the incubation period the bags (three times 1 kg treated seed) are flushed with mechanical washing, interrupted by five centrifuging periods. The wash liquid is checked visually for opalescence and by touch for mucosity. If the wash liquid appears to be clear as water the washing is stopped. From the bags the free water is removed by drainage or centrifugation, and then the content of bags is used for further processing.

EXAMPLE 4

Production of Enzyme Solution by Fermentation 2 liters of first pressure of flax mucilage is added to 8 liters of potato extract and is put into New Brunswick M-100 fermenter. The sterilization is accomplished at 121° C., ~1.2× $10^5$ Pa (1.2 bar) for 40 minutes. After sterilization the fermentation broth is cooled to 25° C. The fermentation broth is inoculated with 100 ml Glyocladium catenulatum inoculum suspension previously grown on shaker machine for 24 hours. In order to grow Glyocladium catenulatum (a microparasitic, but non-plant parasitic fungus producing extracellular enzymes) in the fermenter the regime should be as follows: temperature: 27° C., stirring 150 rpm, pH should be adjusted to 6,5 during the whole fermentation cycle, relative oxygen saturation should be kept at 60%, aeration control should be cascaded from oxygen control. Foam control is necessary during the fermentation. The fermentation regime should be controlled by ML-100 multiloop controller. The fermentation period is 36-48 hours. After finishing the fermentation the whole fermentation broth is centrifuged at 16000 rpm for 40 minutes in a Sorwall High-speed centrifuge. The supernatant is used as enzyme solution. (The pellet could be used as a biological antifungal agent.)

Alternatively 2 ml chloroform is added to 10 litres of supernatant to kill remaining spores and cells, or the supernatant is sterilized by filtration, then the filtrate is allowed to settle for 10 hours at room temperature. In that case if no any sterilization process is used for the supernatant containing enzymes, an additional, repeated sodium hypochlorite treatment of the flax seed is necessary after removal of the mucilaginous material. The enzyme activity could be measured and adjusted according to Kalac J. and Rexova L. (Biochim. Biophys. Acta 167(3): 590-596, 1968).

Further processes are similar to Example 1-3. With this alternative process the production costs in the large-scale industrial production of demucilaged flax sprouts could be significantly decreased.

EXAMPLE 5

Preparation of Demucilaged Flax Sprouts

Holding the seeds perfectly freed of mucilaginous materials in a plastic bag (according to Examples 1-3) are immersed for the purpose of the sterilization of their surface in 5% (w/v) sodium hypochlorite solution for 40 minutes in the course of continuous moving, then the seeds in the bag are flushed twice and drained well. Then the bag is placed in a tray, and the seeds are spread out (within the bag) in a uniform layer. The seeds smoothed down in this manner (about 3 cm thick layer) are incubated in darkness at 18-22° C. for 24-48 hours. Generally the amount of water absorbed by the seeds during the enzymatic treatment and further treatments is enough to start the sprouting and to develop 2-5 mm long sprouts during the incubation period. During the incubation period the seed mass consumes the water adhered on seeds, and normally no further drying is necessary. At the end of the incubation period the ratio between sprouted and non-sprouted seeds are established (300 seed samples can give a correct result). 98-100% of the seeds demucilaged according to Examples 1-3 sprout proving the fact that the demucilaged flax seed are viable. The flax sprouts have a mildly hazelnut taste in this stage, and have no unpleasant by-taste.

As far as the utilization of fresh flax seed sprout produced according to Example 5 is concerned, there are many possibilities. Trials were made in connection with the use of known packing techniques and compared to how long the product obtained according to the invention can be stored. The results of experiments are summarized in the following Table 2.

TABLE 2

Storage of demucilaged fresh flax sprouts at 4° C.

| Package | Evaluation after 30 days | Evaluation after 60 days | Evaluation after 90 days |
| --- | --- | --- | --- |
| Foil filled with normal air | No alteration, original taste | No alteration, original taste | Mild browning, mildly bitter taste |
| Vacuum foil | No alteration, original taste | No alteration, original taste | No alteration, original taste |
| Foil filled with $N_2$ gas | No alteration, original taste | No alteration, original taste | No alteration, original taste |

By packing the product in vacuum foil it is possible to ensure the storability and marketing of product without reduction of quality.

EXAMPLE 6

Use of Demucilaged Flax Sprouts

The flax sprouts prepared according to Example 5 was used freshly or after storage without further treatment.

500 grams of cake-plating, tempered chocolate are melted in a water bath at 32° C., then a chocolate melting mold is formed in a thin layer (about 1 mm thick). Then the chocolate layer is allowed to cool down slightly and to become hard. On this layer 300 g flax sprouts are evenly spread and this layer is again covered with melted chocolate in a manner that the total amount of flax sprout should be covered, while being careful that the temperature of pouring chocolate should not exceed 32° C. After hardening of this layer finally a thin top-layer is poured from chocolate. The product can be stored at least for 60 days in room temperature without reduction of quality.

This example is to show that in the preparation of industrial food products it is necessary to apply such a technology in which the fresh flax sprout is not in contact with air in order to preserve the original values of flaxseed as long time as possible. In the case of milk- and meat products the procedure is similar.

EXAMPLE 7

Preparation of Mildly Dried, Demucilaged Flax Sprouts

The flaxseeds of variety *Linum usitatissimum* cv. Goldenline 90 with high sprouting ability, purified for food industrial purposes (1 kg) are placed into a 10 litre bag made of plastic net with mesh of 0.2 mm. The bag of closed form is placed into 1.5 litres enzyme solution. The composition of enzyme solution is the following.

3 U/ml Pectinase (from *Aspergillus niger*) (Serva)

10 U/ml Glucuronase (Industrie Biologisque Francaise SA)

30 U/ml Sulfatase (Industrie Biologisque Francaise SA)

After 18 hours incubation the flax seeds are to be freed perfectly from the mucilage. The cleaned seeds are sterilised and sprouted according to Example 4. When the size of sprouts become 2-5 mm long (about 18 hours), the sprouted flaxseeds are spread out in a thin layer (at last 1 cm) and they are dried at a temperature less than 30° C. to 85 percent of the initial weight in a usual way or by the help of a mechanical equipment (e.g. vacuum pump). The demucilaged flax sprouts dried in this mild manner can be utilized as they are or as an additive for foods. For example, the chocolate prepared from this product can be stored for 18 months in room temperature.

EXAMPLE 8

Preparation of Grist from Flax Sprouts

From demucilaged flax sprouts dried according to Example 7, a rough preparation is prepared in a quick-blade grinding machine. The quick-blade grinding machines are suitable for this purpose because it can be ensured that during the grinding the temperature does not exceed 30° C. The grist obtained in this manner can be stored for a long time similarly to the grist prepared from cereals.

EXAMPLE 9

Recovering of Mucilaginous Material (By-Product)

The flaxseeds treated according to Example 1-3 perfectly swollen in water and held in bags are put in a press (e.g. wine-press is suitable), then the mass are pressed to such an extent that 90% of mucilaginous material should be pressed out and the seed should not injured. The pressed out, concentrated mucilaginous material is mixed with 96% ethanol in a ratio 1:1. From the about 50-50% water-ethanol solution the mucilaginous material is allowed to precipitate standing at least 12 hours at 4° C. After precipitation the mucilaginous material can be removed by centrifugation (e.g. preparative centrifuge, separator) and the alcohol can be recovered. The precipitate-obtained in this manner is almost dehydrated with 96% alcohol, then the pure precipitate is dried (at 120° C.). After drying a hard amorphous material is obtained, which can be packed and utilized. The thus-obtained mucilaginous material can be completely dissolved in water.

Use of Mucilaginous Material

EXAMPLE 10

10 grams of dried and pulverized mucilaginous material prepared according to Example 9 are solved in 100 ml lukewarm milk. For redissolving the mucilaginous material 30 minutes are necessary at 40° C., and 2 hours are necessary at 15° C. under constant stirring. After dissolution 200 ml fresh yoghurt is added and the mixture is spiced according to the manufacturer's wish. The mixture is whipped to a foam. In this manner 500 ml stable yoghurt foam is obtained which can be stored for 6 days at 4° C. The product also acts as a laxative.

EXAMPLE 11

30 grams of dried and pulverized mucilaginous material are dissolved in 300 ml water at 80° C., 200 ml maize germ oil is added and the mixture is cooled down to 50° C. The mixture is stirred in a homogenizer with high speed rotation, then the white cream obtained in this manner is cooled to 5° C. Into the basic body lotion prepared in this manner any active ingredient can be taken to reach the desired product.

EXAMPLE 12

5-10 grams dried and pulverized mucilaginous material prepared according to Example 9 are added into 1 liter potato extract (the liquid of boiled potato). This mixture is sterilized at 120° C., then after cooling is inoculated *Aspergillus niger* inoculum and the liquid is fermented in a manner known per se. The culture of *Aspergillus niger* is harvested after 48 hours and is processed further.

While the present invention has been described in conjunction with the specific embodiments set forth above, many alternatives, modifications and other variations thereof will be apparent to those of ordinary skills in the art. All such alternatives, modifications and variations are intended to fall within the spirit and scope of the present invention.

The invention claimed is:

1. Mucilage-free flax sprouts obtained from the following steps:
    a) completely demucilaging flaxseed by treating flaxseeds with an aqueous enzyme solution containing at least one pectinolytic enzyme, at least one cellulolytic enzyme, and at least one proteolytic enzyme;
    b) removing mucilaginous material separated from the surface of flaxseeds during the treatment in step a);
    c) applying an oxidizing sterilizing agent on the surface of the flaxseeds resulting from step b) to form sterilized mucilage-free flaxseeds; and
    d) sprouting the sterilized mucilage-free flaxseeds resulting from step c) to obtain mucilage-free flax sprouts.

2. The mucilage-free flax sprouts according to claim 1 in a raw, dried, or dried and ground form.

3. The mucilage-free flax sprouts of claim 1, wherein said enzyme solution comprises a supernatant derived from a fermentation broth of a micro-organism producing an extracellular pectinolytic, cellulolytic, and proteolytic enzyme.

4. The mucilage-free flax sprouts of claim 1, wherein the flaxseeds are soaked in water after the enzymatic treatment in step a).

5. The mucilage-free flax sprouts of claim 1, wherein after the enzymatic treatment in step a) the mucilaginous material is completely removed from the surface of flaxseeds.

6. The mucilage-free flax sprouts according to claim 5, wherein the demucilaged flaxseeds in step c) are sterilized by treatment with sodium hypochlorite solution.

7. The mucilage-free flax sprouts according to claim 6, wherein the sterilized demucilaged flaxseeds in step d) are sprouted at a temperature 18-30° C. for 6-48 hours.

8. The mucilage-free flax sprouts according to claim 1, wherein as a further step the sprouts resulting from step d) are dried to 75-90 percent of the initial seed weight.

9. The mucilage-free flax sprouts according to claim 8, wherein after drying the sprouts are ground and optionally further processed.

10. The mucilage-free flax sprouts according to claim 1 prepared for direct human consumption.

11. The mucilage-free flax sprouts according to claim 1 prepared for food industrial use.

12. A food supplement comprising the mucilage-free flax sprouts according to claim 1.

13. The mucilage-free flax sprouts according to claim 1 prepared for pharmaceutical use.

14. The mucilage-free flax sprouts according to claim 1 prepared for use as a fodder or an additive for fodders.

* * * * *